United States Patent [19]

Polyak

[11] Patent Number: 4,660,244
[45] Date of Patent: Apr. 28, 1987

[54] HYDRAULIC BRUSH FOR TEETH AND GUMS

[76] Inventor: Mark Polyak, 10501 Cedar Lake Rd., Apt. 319, Minneapolis, Minn. 55343

[21] Appl. No.: 751,793

[22] Filed: Jul. 3, 1985

[51] Int. Cl.⁴ .............................................. A46B 13/02
[52] U.S. Cl. ....................................................... 15/24
[58] Field of Search .................... 15/24, 23, 29, 28, 97

[56] References Cited

U.S. PATENT DOCUMENTS

| | | | |
|---|---|---|---|
| 2,283,314 | 5/1942 | Ckola | 15/24 |
| 3,046,585 | 7/1962 | Ledingham et al. | 15/24 |
| 3,553,758 | 1/1971 | Wood | 15/24 |
| 3,909,867 | 10/1975 | Hogsell | 15/24 |
| 4,163,300 | 8/1979 | Quint | 15/23 |

*Primary Examiner*—Edward L. Roberts
*Attorney, Agent, or Firm*—Clayton R. Johnson

[57] ABSTRACT

A hydraulic brush for teeth and gum cleaning and massaging, having a rotating cylindrical, spiral, disc or cupped-shape brush with radially projected ultrathin bristles and simultaneous liquid jets supply to the teeth and gums.

19 Claims, 10 Drawing Figures

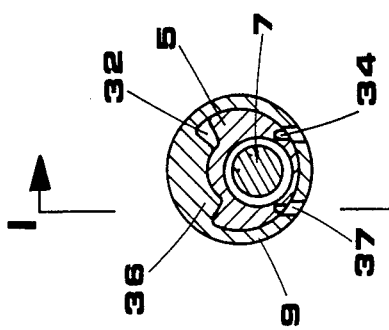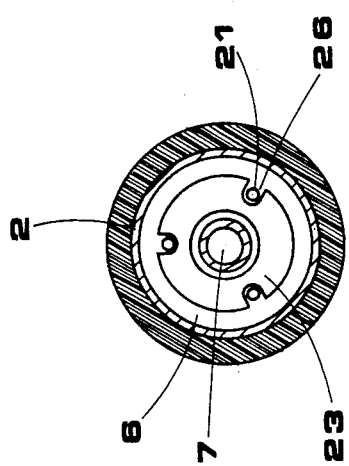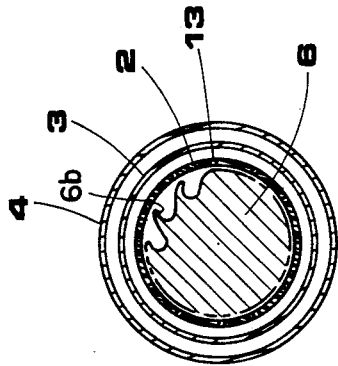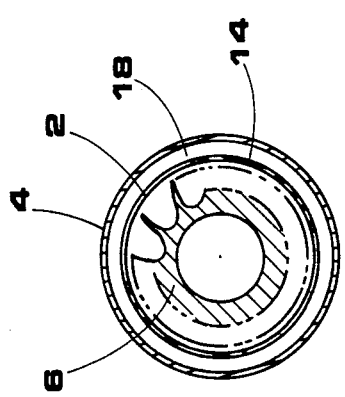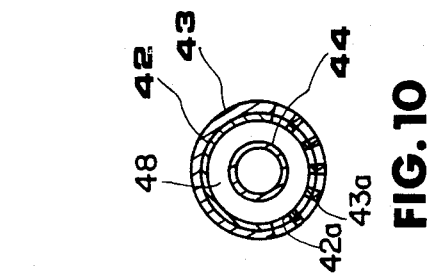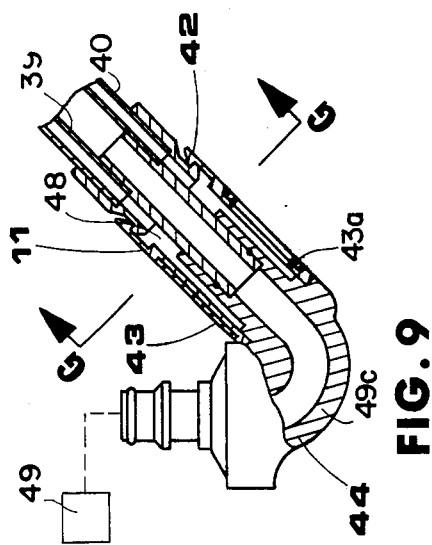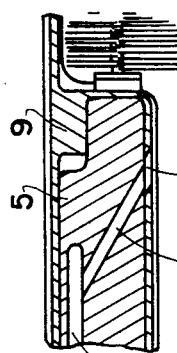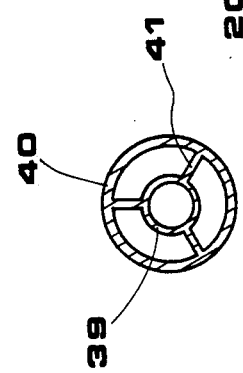

HYDRAULIC BRUSH FOR TEETH AND GUMS

1. BACKGROUND OF THE INVENTION

This invention relates to hydraulically driven devices for teeth cleaning and gum massaging and more particularly to a hydraulically driven toothbrush, which includes a rotating brush with radially projected ultrathin bristles and a simultaneous liquid jet supply to the teeth and gum.

2. DESCRIPTION OF THE PRIOR ART

The prior art discloses a variety of personal hygiene devices, where the power of water under pressure is used to provide a brush with oscillating, swinging, vibrating or reciprocating motions or to supply water jets (water pick) to the teeth and gums. Some are in the form of a separate toothbrush—waterpick assemblies. In either form toothbrushing and water picking are two separate processes and requires either head exchange or device readjustment. Such devices are discloses in U.S. Pat. Nos. 3,809,977 Balamuth; 3,966,359 Woog, 4,257,433 Kwan, 4,319,595 Ulrich. Devices with rotating or oscillating cylindrical or oval toothbrushes are disclosed in U.S. Pat. Nos. 2,184,850 Schloss; 2,655,675 Groves; 2,798,237 Grover; 3,732,589 Burki; 4,320,774 Kogera. Common disadvantages of these devices are: Inefficiency of crevice and gum pocket cleaning and gum massaging because of brush design and bristle size, lack of accessibility to some zones of the mouth, lack of sufficient hydraulic environment in cleaning and massaging zones, absence of continuous wash out of soft and hard debris during toothbrushing, bulkiness and inconvenience in application, complexity with cleaning the brush after toothbrushing, lack of brush speed and power adjustment. The object of this invention is to provide a hydraulic brush for the teeth and gums, which is free of all aforementioned disadvantages.

SUMMARY OF THE INVENTION

In accordance with the present invention the teeth and gum cleaning and massaging are performed by a rotating spiral, cylindrical, disc or cupped-shaped brush with radially projected ultrathin bristles and by simultaneously supplied liquid jets. The brush is rotated by a hydraulic drive. Liquid under pressure, for example water from a pump or from a faucet of a regular running water system, is supplied to the hydraulic drive. The hydraulic drive is connected to a liquid source by a flexible supply tubing, which is located inside of a flexible exhaust tubing. Outside surface portions of the supply tubing and the inside surface portions of the exhaust tubing form a ring-shaped liquid exhaust channel. The brush is rotated by a hydraulic drive and the user can control the brush speed and power. The brush has a lip-tongue protector-valve which can be pivoted between two positions. In one position it turns the liquid jets supply on while the opposite pivoting position turns jet supply off. The hydraulic drive is connected to a source of liquid under pressure by a flexible supply tubing, which is located inside of a flexible exhaust tubing. One end of the exhaust tubing is connected to an outlet orifice of the brush drive and the opposite end to an exhaust valve, which continuously controls the amount of liquid coming to jet-nozzles. Radially projected ultrathin bristles of the rotating brush and the simultaneous liquid jets supply efficiently clean crevices between the teeth, gently massage the gums, remove soft deposits from the gums, getting below the gum line into the gum pockets and selcus, without injuring tender gum tissue. Manual reciprocating motions of the brush removing plaque from the surface of the teeth and also massage the gums. The continuous ability to adjust the brush and jets speed and power allows the user to choose the most sufficient teeth and gum cleaning and massaging parameters. Liquid from an inlet orifice of the hydraulic drive flows through a ring-shaped inlet passage to tangential nozzle-slots of a working chamber. Liquid jets enter through the nozzle-slots into a working chamber and rotate a rotor, a shaft connected to rotate to be driven thereby, and a brush secured on the shafft end. The brush speed and power is proportional to the amount and pressure of the liquid entering the working chamber and because of that can be continuously controlled. If the amount of liquid entering the working chamber is constant, the brush speed is inversely proportional to the force with which the brush is pressed to the teeth and gums by the user. The brushes are exchangeable and disposable. To perform different tasks of the tooth and gum cleaning and massaging, different brush types can be used, such as cylinderical, spiral, disc, cup, etc. Liquid flows from the working chamber through slots located at the rear end of the working chamber into a ring-shaped exhaust passage formed by outside surface portions of the internal cover walls and inside surface portions of the walls of a handle-cover. Moving along the exhaust passage, liquid comes to an outlet orifice of the hydraulic drive and enters the tubing's exhaust channel. The opposite end of the exhaust tubing is connected to an exhaust valve, through which the liquid can be drained into a pump collecting tank for recycling or into a sink sewage system. Part of the liquid from the working chamber via an axial channel is directed to jet nozzles located in a head part of the hydraulic drive. The amount of liquid directed to the jet nozzles is controlled by the exhaust valve. The larger the outlet opening of the discharge valve the smaller amount of liquid coming from the working chamber to the jet nozzles and vice versa. The rotating brush and liquid jets are simultaneously cleaning and massaging the teeth and gums, washing soft and hard debris out of the mouth. The hydraulic brush has a disposable protector-valve pivotally secured on the front cover to protect the lips and tongue from the rotating brush bristles. By pivoting the protector-valve, the liquid jet supply to the teeth and gums can be turned on or off. Because the brushes and protector-valves are disposable and easily interchangeable, different people can use the same hydraulic drive with their personal brushes and protector-valve. This brush provides numerous hygienic features for the most efficient tooth and gum cleaning and massaging possible. These features include a rotating brush with ultrathin bristles, simultaneous liquid jets supply and the ability to continuously adjust the brush speed and liquid jets pressure. Furthermore this brush provides easy access to every zone in the users mouth. Other objects and features of the invention will become apparent from the following detailed description of a preferred, but not limitative embodiment and the accompanying drawings made a part hereof and to which reference is made.

BRIEF DESCRIPTION OF THE DRAWINGS

FIG. 3: A transverse sectional view taken on the line B—B of FIG. 2;

FIG. 4: A transverse sectional view taken on the line C—C of FIG. 2;

FIG. 5: A transverse sectional view taken on the line D—D of FIG. 2;

FIG. 6: A transverse sectional view taken on the line E—E of FIG. 2;

FIG. 7: A transverse sectional view taken on the line F—F of FIG. 2;

FIG. 8: A transverse sectional view taken on the line I—I of FIG. 6;

FIG. 9: A longitudinal sectional view taken on the exhaust valve with half-connector;

FIG. 10: A transverse sectional view taken on the line G—G of FIG. 9.

DESCRIPTION OF THE PREFERRED EMBODIMENT

Figures 1, 2:
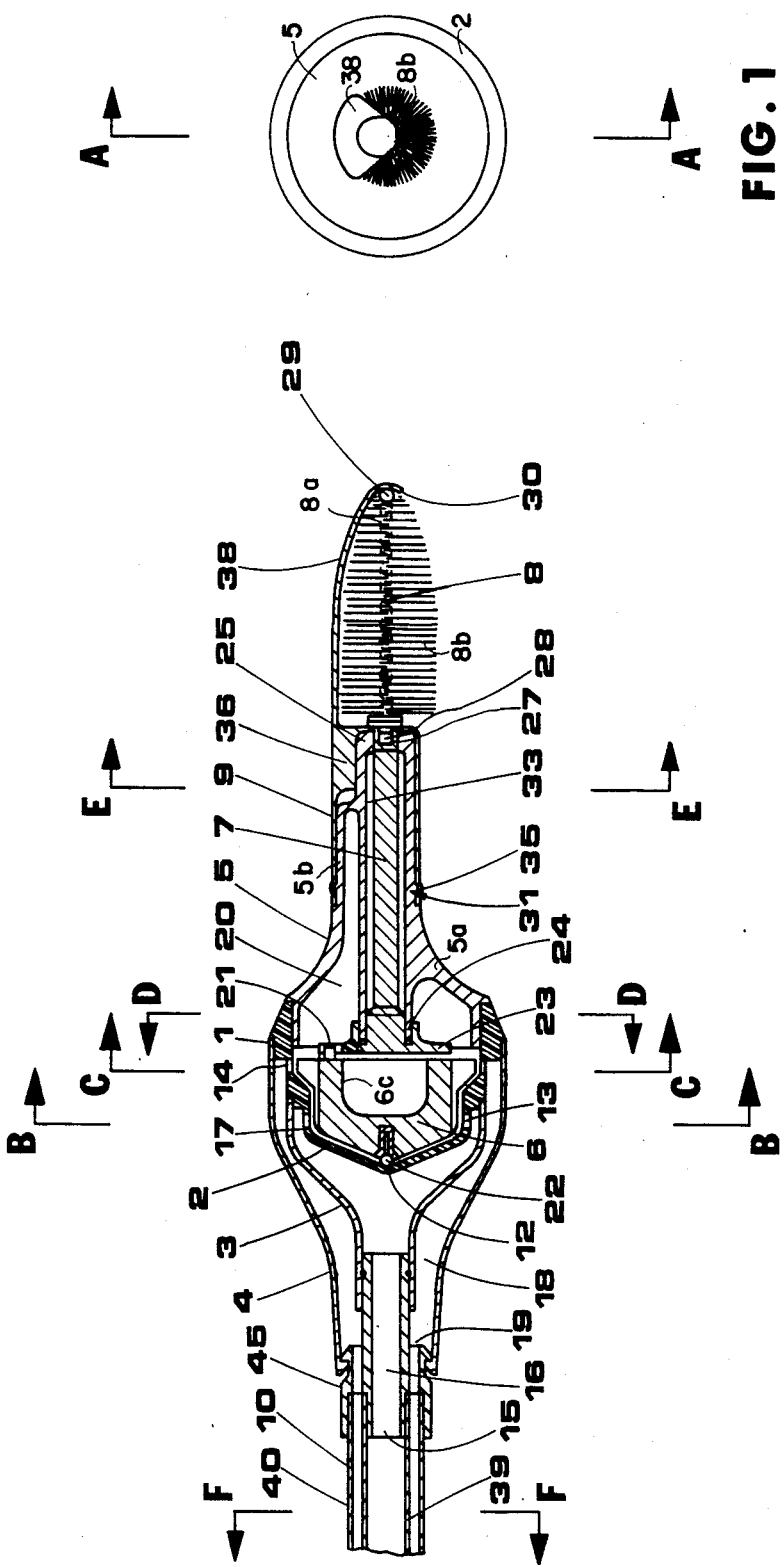
FIG. 1: A front end of the hydraulic brush for teeth and gums.
FIG. 2: A longitudinal sectional view taken on the line A—A of FIG. 1.

Referring now more particularly to the drawings, the hydraulic brush for the teeth and gums according to one embodiment of the invention includes a main housing 1 with a working chamber 2, an internal cover 3 and a handle-cover 4, a front cover 5, a rotor 6, a shaft 7, a brush 8, a protector-valve 9, a flexible supply-exhaust tubing 10, an exhaust valve 11, a connector for the supply-exhaust tubing to a source of liquid under pressure (for example a running water faucet (diagrammatically shown as a box 49. The cylindrical hollow stepped working chamber 2 has a conical front end outside and a truncated conical front end inside with a vertax wall 12. Tangential inlet slots 13 on a front first step circumference and the outlet slots on the rear last step circumference of the working chamber are equally spaced, the circumference of the first step being larger than that of the last step. The internal cover has an inlet orifice 15 and a channel 16. Outside walls of the working chamber first step and inside walls of the internal cover form a ring shaped inlet passage 17 from the inlet orifice 15 through channel 16 to the inlet tangential slots 13. Outside walls of the working chamber and internal cover and inside walls of the handle-cover 4 form an outlet passage 18 from the working chamber outlet slots 14 to an outlet orifice 19. The step-shaped rotor 6 with a conical rear end is freely, without support, located inside the working chamber 2. A freely rotating ball 22 is secured on the rotor conical end tip, forming with the housing vertax wall 12 a one ball thrust bearing. The stepped rotor has a front portion of a larger circumference than its rear portion, the radially extending dimensions of the rotor vane's front portions 6a being greater than the corresponding radially extending dimensions of the rotor vane's rear portions 6b. The rotor has pins 21 equally spaced on its front main body portion 6c to extend forwardly thereof. The shaft 7, flexibly connected with the rotor, is secured in the rear bearing 24 and the front bearing 25 of the front cover 5. There are radial slots 26 equally spaced on a shaft flange 23 that forms a rear portion of the shaft. The pins 21, engaged with slots 26, form a coupling between the rotor and shaft that permits limited axial and radial floating movement of the rotor relative to the shaft and working chamber. An opposite shaft end has a shaped blind hole 27 for the brush installation. To perform different tasks in everyday tooth and gum care, sets of different types of exchangeable and disposable brushes can be used with the same hydraulic drive. For example a wiretwisted spiral brush 8 with ultrathin—0.003-0.005" dia. radially projected bristles 8a has a shaped adapter 28, fixed on a twisted wire brush core 8b and a ball 29 also fixed on the core. To secure the brush on the shaft 7 the adapter 28 should be inserted into the shaft hole 27 formed in the front end portion of the shaft. The front cover 5 has a hollow elongated cylindrical part 5b with an annular bead 31, wall portions defining a radially outwardly, forwardly opening rectangular notch 32, a longitudinal hole 33 between bearings 24 and 25, an axial channel 20 and inclined jet nozzles 34 in it's front portion to discharge liquid adjacent to the rear portion of the brush in a direction forwardly and generally away from the front part 38 of the protector-valve. An axial line (central axis) of the elongated cylindrical part is offset against an axial line (central axis) of the front cover body 5a and bearing 24 and 25, the axis of rotation of the shaft and the brush being coextensive with the central axis of the body 5a and the bearings 24 and 25. As may be seen from FIGS. 2 and 6, the protector-valve rear portion has a circular outer peripheral surface that has a radius of curvature eminating from the cylindrical portion central axis. The disposable protector-valve 9, pivotally mounted on the elongated cylindrical part of the front cover has a ring groove 35, a tooth 36, slots 37, an arch front part 38 with halfspherical hole 30. The groove 35 in having the annular bead portion 31 of the part 5b extend therein secures the protector-valve on the front cover and the tooth 36 in being located in the notch 32 restricts the pivoting angle of the protector valve on the front cover. At one extreme pivoting position the slots 37 coincide with the jet nozzles 34 and turn the liquid jets supply on. At the opposite pivoting position the protector-valve walls block the nozzles and shut the jets off. The brush ball end 29 with the halfspherical hole 30 form one ball brush support bearing. The front arch part 38 of the protector-valve is transversely arcuately curved about an angular portion of the brush to guard the lips and tongue from the rotating brush bristles. The combined supply-exhaust flexible tubing 10 consists of a smaller diameter supply tubing 39, located inside of a bigger diameter exhaust tubing 40 and connecting them webs 41. One end of the flexible supply tubing is connected via connector 45 to the inlet opening 15 of the internal cover 2 and the opposite end is connected to a quick coupling 44. One end of the exhaust tubing 40 is connected to the handle-cover 4 by the connector 45. The opposite end of the exhaust tubing is connected to the valve housing 42 of the exhaust valve 11. The housing 42 is secured on the quick coupling 44 and has slots 42a. The drum 43 is pivotly installed on the housing 44 surrounds a tubular portion of the quick coupling that is connected to tubing 39 to provide an annular clearance space 48 and also has slots 43a. The housing and drum slots form an outlet opening through which liquid drains from clearance space 48 into a sewage system or into a pump collecting tank for recycling. The size of the exhaust valve outlet opening is adjustable by pivoting the drum around the housing. The pressure in the brush drive exhaust system is adjusted by changing the outlet opening size of the exhaust valve.

Pressurized liquid from a source, for example, a running water faucet flows through a quick coupling 44, supply tubing 39, inlet orifice 15 and channel 16, coming to the ring shaped inlet passage 17. Water jets, entering the first stage of the working chamber 2 through tangential slots 13, rotate the rotor which through the shaft 7 rotates the brush 8. From the first stage of the working chamber water moves through the next stages and then emerges through the outlet slots 14 into the outlet passage 18 and via outlet orifice 19, exhaust tubing 40 and the exhaust valve outlet slots drains into a sink sewage system. Part of the water from the working chamber flows through the axial channel 20 to the nozzles 37 and comes out from the nozzles at a location adjacent to the rear part of the brush as water jets. The amount of water coming from the working chamber to the nozzles is inversely proportional to rotor's rotating speed and the opening size of the exhaust valve. The lower the brush speed and the smaller an opening of the exhaust valve the bigger amount of liquid comes out of the nozzles.

Yet, although the showing of FIG. 2 conveniently summarizes many of the features of the present invention and, although other numerous characteristics and advantages of the present invention, together with details of the structure and function, have been described in detail, it is to be understood that the disclosure is illustrative only. Consequently, any changes made, especially in matters of shape, size and arrangement, to the full extent extended by the general meaning of the terms in which the appending claims are expressed, are within the principal of the invention.

I claim:

1. Liquid operated apparatus adapted for connection to a source of liquid under pressure for cleaning teeth and gums, comprising a rotor rotatable by liquid flow, a main housing having a front end, a rear end, means defining a working chamber that has a working chamber interior with the rotor rotatably mounted therein, an internal cover and a handle cover connected to the means defining the working chamber to form an inlet passage opening to the chamber interior to supply liquid under pressure for rotating the rotor and an outlet passage opening to the working chamber interior for conducting liquid away from the working chamber interior, a shaft connected to the rotor for being rotated thereby, said shaft having a rear end adjacent to the rotor and a front end, a brush having an axis of rotation connected to the shaft, elongated means mounted by the housing to extend forwardly thereof to mount the shaft for rotation, extend forwardly at least the axial length of the brush and angularly partially around the brush to guard the lips and tongue of the user and discharge jets of liquid toward the teeth during use to aid in cleaning the teeth, the elongated means having a liquid jet discharge opening adjacent to the brush for discharging liquid as a jet and a jet liquid passage opening to the working chamber interior for conducting fluid from the working chamber interior to the jet discharge opening, a coupling having a supply passage adapted to be connected to the source of liquid under pressure and means for fluidly connecting the coupling supply passage to the inlet passage and fluidly connected to the outlet passage for conducting liquid adjacent to the coupling to discharge liquid adjacent to the coupling at selectedly adjusted rates to thereby control the rate of discharge of liquid through said jet discharge opening and the speed of rotation of the rotor.

2. The apparatus of claim 1 further characterized in that the means for fluidly connecting the coupling includes means for forming an exhaust valve opening and means for selectively varying the effective size of the valve opening to control the amount of liquid discharging from the jet discharge opening in inverse relationship to the speed of rotation of the rotor.

3. The apparatus of claim 1 further characterized in that said elongated means includes a front cover connected to the housing to extend forwardly thereof and having said jet liquid passage which includes an inlet end portion opening to the working chamber interior and a discharge end portion, and a protector-valve having the jet liquid discharge opening mounted on the front cover for pivotal movement between a position permitting liquid to flow through the discharge end portion and be discharged throught the jet liquid discharge opening and a closed position blocking the discharge of liquid from the discharge end portion through the jet liquid discharge opening.

4. The apparatus of claim 1 further characterized in that the coupling includes a tubular portion fluidly connected to the inlet passage and that the means for fluidly connecting the coupling includes an annular valve housing surrounding the tubular portion to provide a clearance space therebetween that is in liquid communication with the outlet passage, a drum mounted on the valve housing, said valve housing and drum having outlet slots for forming an outlet opening to drain liquid from said clearance space, the drum being pivotable relative to the valve housing from a position the drum slot is aligned with the housing slot to an out of aligned position for continuously controlling the size of the last mentioned opening.

5. The apparatus of claim 1 further characterized in that the means defining the working chamber comprises a hollow cylindrical portion having a front end and a rear end, and a conical rear wall joined to the cylindrical portion rear end and having a vertex portion located further rearwardly than the cylindrical portion rear end and that the rotor has a concical tip rear portion and a ball freely rotatably mounted by the conical tip rear portion in abuttable relationship to the vertex portion.

6. The apparatus of claim 5 further characterized in that the cylindrical portion has a front cylindrical part and a rear cylindrical part of a smaller inner diameter than the front cylindrical part, the front cylindrical part having equally spaced outlet slots extending therethrough, the rear cylindrical part having equally spaced tangential inlet slots extending therethrough, the inlet passage opening to the inlet slots and the outlet slots operning to the outlet passage, and that the rotor has front vane portions located within the rear cylindrical part and rear vane portions located within the rear cylindrical part, the front vane portions being of greater radially extending dimensions than the corresponding dimensions of the rear vane portions.

7. The apparatus of claim 5 further characterized in that the rotor is mounted in the working chamber without radial support and has a front main body portion and a plurality of circumferentially spaced pins mounted by the front main body portion to extend forwardly thereof and that the shaft has a rear flange portion adjacent to the rotor main body portion, the rear flange portion having a plurality of circumferentially spaced slots for the pins to extend into for drivingly rotating the shaft and permit limited floating movement to the rotor relative to the shaft.

8. The apparatus of claim 1 further characterized in that the elongated means includes an elongated arch shaped front part that extends angularly partially around the brush to protect the lips and tongue from the rotating brush, the arch shaped front part having a front end portion located a substantial distance forwardly of the shaft front end, the arch shaped front part having a partial speherical hole, and that the brush includes a brush core having a front end and a rear end, a ball mounted by the brush front end and extended into the partial spherical hole, and an adaptor fixed to the brush rear end for attaching the brush core to the shaft front end.

9. The apparatus of claim 8 further characterized in that the elongated means includes a front cover that has an elongated front cylindrical part which has a central axis and a bearing that in part mounts the shaft for rotation, the axis of rotation of the shaft being offset from the cylindrical part central axis, the arch shaped part being mounted on the cylindrical part to extend forwardly thereof, that the brush core is made of twisted wires and that the brush includes ultra-thin bristles projecting radially from the brush core and that the means for fluidly connecting the coupling includes an exhaust tubing and a supply tubing located within the exhaust tubing, and webs extending between the tubings, the supply tubing forming a part of the inlet passage and the exhaust tubing and supply tubing having a space therebetween that forms a part of the outlet passage.

10. The apparatus of claim 1 further characterized in that the elongated means includes a front cover that has bearings for rotatably mounting the shaft, and the passage for conducting liquid from the working chamber to the jet discharge opening, said front cover having a rear end mounted by the main housing and a front cylindrical portion that has a front end and a passage outlet adjacent to the cylindrical portion front end that forms a part of the passage for conducting liquid to the jet discharge opening.

11. The apparatus of claim 10 further characterized in that the elongated means includes a protector-valve that is mounted on the front cover for limited pivotal movement to protect the lips and tongue during rotation of the brush and to selectively permit discharge of liquid through the passage outlet and alternately block the flow of liquid through the passage outlet to the discharge opening.

12. The apparatus of claim 11 further characterized in that the front cylindrical portion includes wall portions that define a radially outwardly and forwardly opening notch and that the protector-valve has a tooth extended into the notch and movable relative to said wall portions to limit the pivotal movement of the protector-valve relative to the front cover.

13. The apparatus of claim 11 further characterized in that the shaft and brush have an axis of rotation, that the protector-valve has an arcuately curved portion located in radial spaced relationship to the brush that extends arcuately only partially around the brush, the passage for conducting liquid to the jet discharge opening includes a jet nozzle in the cylindrical portion that is inclined in a direction to discharge liquid in a jet that is directed forwardly and generally away from said arcuate portion.

14. The apparatus of claim 13 further characterized in that the cylindrical portion has a central axis offset from said axis of rotation, that the coupling has a tubular portion that defines a part of the coupling supply passage, and that the means for fluidly connecting the coupling includes an annular valve housing that at least in part surrounds the coupling tubular portion to provide a clearance space therewith that the outlet passage opens to, the valve housing having a valve discharge opening that opens to the clearance space, and means mounted on the valve housing for movement relative thereto for selectively varying the rate of discharge through the valve housing discharge opening.

15. Liquid operated apparatus adapted for connection to a source of liquid under pressure for cleaning teeth and gums, comprising a rotor rotatable by liquid flow, a housing having a front end, a rear end and means defining a working chamber that has a working chamber interior with the rotor rotatably mounted therein, an inlet opening for liquid to flow into the interior to rotate the rotor and an exhaust opening for exhausting liquid from the working chamber interior, the means defining the working chamber including a hollow cylindrical portion having a front end and a rear end, and a conical rear wall joined to the cylindrical portion rear end and having a vertex portion located further rearwardly than the cylindrical portion rear end, a shaft having a front end and a rear flange portion adjacent to the rotor, the flange portion having a plurality of circumferentially spaced slots and the rotor having a conical tip rear portion, a ball freely rotatably mounted by the tip portion in abuttable relationship to the vertex portion, a front main body portion and a plurality of circumferentially spaced pins joined to the main body portion to extend forwardly and into the flange slots to drivenly rotate the shaft while permitting limited floating movement of the rotor relative to the shaft, and a brush connected to the shaft for being rotated thereby and extend forwardly of the shaft, and means connected to the housing front end for rotatably mounting the shaft, the housing having means for conducting liquid to the working chamber inlet and away from the working chamber outlet.

16. The apparatus of claim 15 further characterized in that the cylindrical portion has a front cylindrical part and a rear cylindrical part of a smaller inner diameter than the front cylindrical part, the front cylindrical part having outlet slots extending therethrough, the rear cylindrical part having tangential inlet slots extending therethrough, the inlet passage opening to the inlet slots and outlet slots opening to the outlet passage, and that the rotor has front vane portions located within the front cylindrical part and rear vane portions located within the front cylindrical part and rear vane portions located within the rear cylindrical part, the front vane portions being of greater radially extending dimensions than the corresponding dimensions of the rear vane portions.

17. The apparatus of claim 15 further characterized in that the shaft and brush have an axis of rotation, that the brush extends forwardly of the shaft, that the means for rotatably mounting the shaft has a liquid passage for conducting liquid from the working chamber interior to adjacent to the brush and discharging the liquid as a jet adjacent to the brush in a direction forwardly and away from the axis of rotation, and that there is provided passage means connected to the housing means for defining an inlet passage for supplying liquid that is conducted to the working chamber and an outlet passage for conducting liquid away from the housing means to be discharged and valving means in fluid communication with the outlet passage for discharging liquid from the outlet passage and selectively varying the rate of discharge from the outlet passage to control the speed of rotation of the rotor and the rate of discharge of liquid as a jet.

18. Liquid operated appartatus adapted for connection to a source of liquid under pressure for cleaning teeth and gums comprising a rotor rotatable by liquid flow, a housing having a front end, a rear end, means defining a working chamber that has a working chamber interior, an inlet opening for liquid to flow into the working chamber interior to rotate the rotor and an exhaust opening for exhausting liquid from the working chamber interior outlet and means defining an inlet passage in fluid communication with the inlet opening to supply liquid thereto and an outlet passage in fluid communication with the outlet opening for conducting liquid away from the means defining the working chamber, the rotor being mounted in the working chamber interior, a shaft having a front end portion and a rear end portion in drivenly rotatable relationship with the rotor, a brush having an axis of rotation, a front end and a rear end portion in driven relationship with the shaft front end portion, a front cover having a front end portion and a rear end portion mounted by the housing to extend forwardly thereof, and protector means mounted by the front cover for protecting the tongue and lips as the brush is rotated, the protector means having an arcuately shaped portion to extend forwardly of the front cover to at least the front end of the brush and partially around the brush, the front cover mounting the shaft for rotation and having a jet liquid passage opening to the chamber interior for conducting the liquid therefrom and a jet nozzle opening to the jet liquid passage and through the cover front portion and adjacent to and rearwardly of the brush to discharge liquid as a jet, the jet nozzle being inclined to extend forwardly and transversely of the jet liquid passage to discharge liquid forwardly and transversely away from the arcuately shaped portion and away from the brush axis of rotation.

19. The apparatus of claim 18 further characterized in that the protector means has a valving portion pivotally movable on the front cover between a position blocking the front cover front nozzle to prevent discharge of liquid as a jet and a position permitting the discharge of liquid as a jet.

* * * * *